United States Patent [19]

Grimm et al.

[11] Patent Number: 5,188,834
[45] Date of Patent: Feb. 23, 1993

[54] METHOD OF PREPARING A BIOLOGICAL IMPLANTATION MATERIAL

[75] Inventors: Michael Grimm; Elisabeth Eybl; Andrea Griesmacher; Martin Grabenwoger; Mathias M. Muller; Ernst Wolner, all of Vienna, Austria

[73] Assignee: Sorin Biomedica S.p.A., Vercelli, Italy

[21] Appl. No.: 530,634

[22] Filed: May 30, 1990

[30] Foreign Application Priority Data

May 31, 1989 [AT] Austria ................... 1323/89

[51] Int. Cl.$^5$ ................ A61F 2/02; A61K 31/115; A61K 31/195
[52] U.S. Cl. ................... 424/422; 424/423; 514/693; 514/694; 514/695; 514/561; 623/11; 523/105; 523/122; 523/113
[58] Field of Search ......... 424/405, 423, 422; 514/693, 694, 695; 523/105, 113, 114, 115, 122; 422/1, 30, 36; 8/94.21, 94.11, 94.20; 623/1, 2, 11, 13; 134/110

[56] References Cited

U.S. PATENT DOCUMENTS

| Re. 33,625 | 7/1991 | Wright et al. ............... 134/110 |
| 4,120,649 | 10/1978 | Schechter ..................... 8/94.11 |
| 4,404,181 | 9/1983 | Mauthner ........................ 424/3 |
| 4,597,766 | 7/1986 | Hilal et al. ..................... 623/13 |
| 4,647,283 | 8/1987 | Carpentier et al. ............ 8/94.11 |
| 4,648,881 | 3/1987 | Carpentier et al. ............ 623/11 |
| 4,786,287 | 11/1988 | Nashef et al. .................. 8/94.21 |
| 4,800,603 | 1/1989 | Jaffe .............................. 8/94.11 |
| 4,838,888 | 6/1989 | Nashef ..................... 8/94.11 X |
| 4,885,005 | 12/1989 | Nashef et al. ................. 8/94.11 |

FOREIGN PATENT DOCUMENTS

| 0089145 | 3/1983 | European Pat. Off. . |
| 0174737 | 3/1986 | European Pat. Off. . |
| 2306707 | 4/1976 | France . |
| WO84/01879 | 5/1984 | PCT Int'l Appl. . |
| 2075819 | 11/1981 | United Kingdom . |

OTHER PUBLICATIONS

Journal of Biomedical Materials Research, vol. 14, pp. 752-764 (Nov. 1980).

Primary Examiner—Thurman K. Page
Assistant Examiner—Neil S. Levy
Attorney, Agent, or Firm—George P. Hoare, Jr.

[57] ABSTRACT

Method of preparing a fixed biological implantation material in which an implantation material is fixed with an aldehyde and the excess aldehyde is bound by an aminodicarboxylic acid in an acidic medium.

7 Claims, No Drawings

METHOD OF PREPARING A BIOLOGICAL IMPLANTATION MATERIAL

FIELD OF THE INVENTION

The invention relates to a method for the preparation of a biological implantation material, wherein the implantation material is fixed with aldehydes, and the excess aldehydes are bound by an aminodicarboxyclic acid.

BACKGROUND OF THE INVENTION

Surgical implantation of biological materials is a frequently employed technique and finds application in many areas of medicine. The material may originate from the recipient himself (autologous tissue), from the same species as the recipient (homologous tissue), or heterologous tissue). Examples of such biological materials are cardiac valves, pericardium, sinews, tendons, ligaments, dura mater, bones, skin, collagen, arteries, veins, etc. Various methods, which reduce the implant these materials as a replacement for or repair of certain defects in man since in the absence of appropriate pretreatments, the biological materials can lead to rejection reactions in man.

Methods of reducing antigenicity mainly have the intent of fixing, that is, denaturing the tissue. For this purpose, these materials are treated with aldehydes, such as glutaraldehyde, formaldehyde and glyoxal. Glutaraldehyde and formaldehyde are the reagents used most, since they are known to have a sterilizing effect. Moreover, they are known to have a good denaturing effect, that is, they reduce the antigenicity of the material to such an extent, that rejection reactions no longer occur after implantation. However, the aldehyde residues present in the tissue must be removed as completely possible, since the aldehydes can cause severe irritations, such as inflammatory reactions or other harmful effects, after implantation. For this purpose, the biological materials are treated before implantation with sterile solutions, such as doubly distilled (oil) water, or with isotonic salt solutions, in order to remove the residues of unbound aldehydes.

It is also already known to remove the aldehydes by the addition of aminodicarboxylic acids. The aldehyde removal reaction is carried out in a medium having a pH greater than 7. These methods, moreover, are based on the principle of a Schiff's base reaction between free, diffusible aldehydes in the tissue and the $NH_2$ groups of the added substance. As the pH increases, Schiff's base reaction. For this reason, care is always taken to ensure that the reaction is conducted in an appropriately neutral to alkaline medium. Aside from aminocarboxylic acids, primary, secondary and tertiary amines, as well as mixtures of these amines are suitable for these reactions.

Such methods, however, still leave significant amounts of aldehyde in the tissue. As a result, the remaining aldehydes, can cause an inflammatory reaction.

It is therefore an object of the invention to provide a method of removing aldehydes from biological materials to the extent that they no longer cause irritation in adjacent tissue.

SUMMARY OF THE INVENTION

In accordance with the present invention, there is disclosed a process for the treatment of a fixed implantation material in the presence of an aminodicarboxylic acid in an acidic medium, preferably at a pH in the range from 2.5 to 5.5 and most preferably from 3 to 5. In this method, the formation of Schiff's bases is prevented because the process is carried out at an acidic pH. This results from the fact that positively charged amino groups are not capable of forming Schiff's bases. In the present invention, the amino groups of said acids, because of their $pk_a$ values, are present in a positively charged state. Instead of Schiff's bases, N,O-hemiacetals are formed in this pH range and are converted into N,N-acetals by an excess of amino groups. Moreover, the hemiacetals, which were formed between collagen (OH groups of lysine, threonine and hydroxyproline) and glutaraldehyde, are converted by acid catalysis into the more stable acetals.

If glutaraldehyde is used for the fixation, then monomeric, linear glutaraldehyde in aqueous solution is in equilibrium with three hydrated linear or cyclic compounds. Moreover, various oligomeric and polymeric forms are also known. They can be attributed to aldol condensations or to a water-catalyzed polymerization of the aldehyde. This chemical heterogeneity of the glutaraldehyde explains the complex reaction mechanism with proteins, as for example, with collagen. The high reactivity of glutaraldehyde is chain length for forming transverse intermolecular cross-links and the possible stabilization by cyclic monohydrates of glutaraldehyde. Despite these investigations, it has not yet been possible to glutaraldehyde and proteins. As is well known, the cross-linking effect of glutaraldehyde on collagen is greatest in an alkaline medium, so that the cross-linking of proteins with glutaraldehyde can be attributed to a formation of Schiff's bases. The polymerization products described largely participate in the toxic effects of aldehyde-modified biomaterials. Due to their increased degree of polymerization and due to the tight mesh, cross-linked collagen structure, these products cannot efficiently diffuse out, so that they can become active again after surgical implantation.

The low pH value, used pursuant to the present invention, splits the polymers of glyceraldehyde into their starting monomeric form. This is accompanied by a reduction in the formation of toxic polymerization products and induces an intensified diffusion. Moreover, due to the splitting of the polymerization products, all free aldehyde groups, that is all aldehyde groups not involved in cross-linking, can be caused to react with the aminodicarboxylic acids.

Aminodicarboxylic acids are particularly suitable for the present process because these acids additionally cross-link with the collagen and therefore form stabilizing bonds. These bonds are formed not by Schiff's bases, but by esters resulting from the free OH groups of the collagen and the acid, and by acetals and hemiacetals. Moreover, the aminodicarboxylic acids can form salt bonds with the free groups of the collagenous tissue. In this case, the salt bonds greatly increase the biocompatibility of the surface of implanted product.

The biological toxicity of the residues of free, unbound glutaraldehyde remaining in the tissue, can be tested in vitro by means of cell tissue cultures. The biological tissue is removed according to known methods, prepared in a customary manner and then subjected to a fixation or sterilization procedure. By means of these tests, it is possible to observe an appreciable reduction of the toxic effects caused by the aldehydes, if the implantation materials are treated according to the present inventive method.

The biological toxicity of the residues of free, unbound glutaraldehyde remaining in the tissue, can be tested in vitro by means of cell tissue cultures. The biological tissue is removed according to known methods, prepared in a customary manner and then subjected to a fixation or sterilization procedure. By means of these tests, it is possible to observe an appreciable reduction of the toxic effects caused by the aldehydes, if the implantation materials are treated according to the present inventive method. The reduction in the toxic effects is significantly superior to that achieved with all previously known methods.

DETAILED DESCRIPTION OF THE INVENTION

Pursuant to the present invention, aminodicarboxylic acids are used to treat fixed implantation materials. The desired pH range is therefore achieved automatically, when the aminodicarboxylic acids are dissolved in sterile distilled water or doubly distilled water. According to the present method, the aminodicarboxylic acids, (such as, for example, glutamic acid, aspartic acid, and isomers and mixtures thereof) are also used in such a manner, that the treatment of the fixed implantation material is undertaken in a buffered medium. Preferably, the following buffer systems are employed: sodium citrate/HCl buffer, citrate-phosphate-borate/HCl buffer or acetate buffer. It is, however, also possible to use other buffers, which do not contain an amino group or do not cause a toxic reaction, which would impair the effectiveness of the present method.

Moreover, if the aldehydes are allowed to react for about 72 hours, the treatment with the aminodicarboxylic acid can be carried out for at least 2 hours at a constant temperature, particularly at a temperature between 4° and 45° C. By these means, an effective decrease in the free aldehyde groups in the tissue is achieved, since the reaction time is sufficiently long to permit diffusion of the aldehyde residues present in the tissue.

The amount of the amino acid used can vary. However, it is preferred to use 0.001 M to 2 M of aminodicarboxylic acids in the treatment solution. The concentration depends to a large extent on the implementation of the post-fixation treatment, since there is a close correlation between the concentration of the amino acid solution, the number of washings, the duration of the reaction and the volume of the aminodicarboxylic acid solution. For example, a shortening of the reaction time while keeping the concentration of the amino acid solution constant would impair the toxicity reducing effect of the aldehydes. A concentration of amino acids, which corresponds approximately to a 10-fold excess compared to the free aldehyde groups, is preferable under these circumstances.

An advantage of the present invention, is that the aminodicarboxylic acids have an extremely low toxicity, so that the implantation material can be implanted directly after the amino acid treatment. After the amino acid treatment, however, it is advisable to carry out at least one washing in an isotonic solution. Any residues of other materials, such as buffers, etc., can also be washed out of the material.

Since the all of the aldehydes are washed out, the implantation material, after the treatment with the aminodicarboxylic acid, can be stored for long periods in a sterile condition, preferably in a biologically tolerated sterilization solution such as Paraben. Manipulating the biological materials should therefore also take place under sterile conditions. A manipulation in a laminar flow of air has proved to be most suitable. It is advantageous to store the implantation material in a sterile Paraben solution (0.02% n-propyl p-hydroxybenzoate and 0.18% methyl p-hydroxybenzoate, dissolved in phosphate buffered salt solution), because this the material. In selecting a storage solution, the toxicity of the chemical used for the solution is important since toxic chemicals can appreciably impair the effectiveness of the present invention. The use of storage solutions other than sterile 0.9% salt solutions, however, presupposes that the biological materials are subjected to at least one washing before the surgical implantation, in order to remove any biologically incompatible chemicals of the storage solution from the tissue.

The present invention is explained in greater detail by means of the following examples. In the Tables that appear, the samples, which have been treated according to the present invention are labeled with an E.

The examples include a comparison with several known methods, which were conducted parallel with the present method, in order to clearly emphasize the difference between the known methods and the inventive method.

EXAMPLE 1

Bovine pericardium from calves was obtained at the local slaughterhouse and immediately placed in an ice-cold 0.9% salt solution. The preparation of the material in the laboratory commenced within one hour. The pericardium was thoroughly freed from excess fatty and connective tissue, under an ice-cold salt solution. The pericardium was then placed in a 0.5% glutaraldehyde solution (pH 7.4) and kept for 24 hours at 4° C.

After this period, the material was cut up into 1 cm$^2$ pieces under sterile conditions in a laminar air flow and divided up into different groups.

1) The pieces were either transferred immediately to a storage solution (0.25% glutaraldehyde solution or Paraben solution) for storage of up to several weeks, or subjected to a 24-hour post-fixation treatment. At the conclusion of this post-fixation treatment, the thus treated materials were stored in an aldehyde-free solution, such as a Paraben solution.

The post-fixation treatment extended over a period of 24 hours and all treatments were carried out at room temperature in accordance with the following procedure using 10ml of a postfixation solution per 1 cm$^2$ of tissue:

a) phosphate-buffered saline (PBS) without calcium and and magnesium
b) 0.5% solution of ammonia (NH$_3$) in distilled water.
c) fetal bovine serum
d) 4% guanidinium chloride solution (GCL) in PBS (pH 7.35)
e) 4% guanidinium chloride solution (GCL) in PBS (pH 7.35) followed by a 10-minute treatment in 1% sodium borohydride (NaBH$_4$)
f) 4% glycine solution in PBS (pH 7.35)
g) 4% glycine solution in distilled water (pH 3)
h) 4% glutamic acid solution in PBS (pH 7.35)
i) 4% glutamic acid solution in distilled water (pH 3)
j) 4% glutamic acid solution in PBS (pH 7.35), followed by a 10-minute treatment in 1% sodium borohydride (NaBH$_4$)
k) 4% aspartic acid solution in PBS (pH 7.35)
l) 4% aspartic acid solution in distilled water (pH 3)

2) After this procedure, the resulting biomaterials, were kept for at least 1 month and then subjected to an in vitro test.

In this in vitro test method, bovine aortal endothelium cells were cultured on the materials. This method provides the most accurate information concerning toxic effects, which were evoked by chemically modified biomaterials, since the cells are cultured in direct contact with the materials. The culturing of bovine aortal endothelium cells is carried out by a standard method. Before the cells were disseminated, the materials were subjected to different washings in order to remove the storage solutions. The amount of washing medium used was 20 ml per 1 cm² piece.

The following were used as washing media:
0.9% salt solution (NaCl) Heilmittelwerke Wien i
human serum
fetal bovine serum (Gibco)

After the various washings, all valvular cusps were placed in 24-hole plates and covered for 4 hours with human fibronectin. The cells were applied with a primary dissemination density of 35,000±9,800 on the materials. The cells were cultured on the materials for a period of 10 days. On the 3rd and 10th days after dissemination, a cell count was taken. For this purpose, the cells were detached from the materials by means of collagenase type I and stained with crystal violet. The cell count, which is given as the cell count per cm², was determined in a hematocyte counter. Controls were run parallel to all the experiments. The 24-hole plate.

The tox score is a description of the toxic effect on cell growth at the time of the cell count, and depends on observations of the integrity of the cell membrane under a scanning electron microscope.

V=extremely toxic
IV=very toxic
III=moderately toxic
II=hardly toxic
I=not toxic Each of the materials named was tested in duplicate (Tables 1 and 2) in 5 different series and the cell count was given as an average value.

TABLE 1

| FIXATION | AFTERTREATMENT | STORAGE | WASHING | CELL COUNT 3rd day | TOX |
|---|---|---|---|---|---|
| 72 h 0.5% GA* | *** | 0.25% GA | 3 × 10 min NaCl | 0 | V |
| 72 h 0.5% GA | | 0.25% GA | 3 × 10 min PBS | 0 | V |
| 72 h 0.5% GA | | 0.25% GA | 3 × 10 min HS | 0 | V |
| 72 h 0.5% GA | | 0.25% GA | 3 × 1 d NaCl | 0 | V |
| 72 h 0.5% GA | | 0.25% GA | 3 × 1 d PBS | 1,035 | IV |
| 72 h 0.5% GA | | Paraben | 3 × 10 min NaCl | 5,450 | IV |
| 72 h 0.5% GA | PBS pH 7 | Paraben | 3 × 10 min NaCl | 9,760 | IV |
| 72 h 0.5% GA | PBS | Paraben | 3 × 10 min NaCl | 9,340 | IV |
| 72 h 0.5% GA | 0.5% NH3 | Paraben | 3 × 10 min NaCl | 7,540 | IV |
| 72 h 0.5% GA | 4% GCl pH 7 | Paraben | 3 × 10 min NaCl | 25,670 | III |
| 72 h 0.5% GA | 4% GCl pH 7 10 min 1% NaBH4 | Paraben | 3 × 10 min NaCl | 24,900 | III |
| 72 h 0.5% GA | 4% Glycine pH 7 | Paraben | 3 × 10 min NaCl | 34,070 | II |
| 72 h 0.5% GA | 4% Glycine pH 3 | Paraben | 3 × 10 min NaCl | 32,980 | II |
| 72 h 0.5% GA | 4% GS pH 7 | Paraben | 3 × 10 min NaCl | 29,890 | III |
| 72 h 0.5% GA | 4% GS** pH 3 | Paraben | 3 × 10 min NaCl | 57,980 E | I |
| 72 h 0.5% GA | 4% GS pH 9 10 min 1% NaBH4 | Paraben | 3 × 10 min NaCl | 33,980 | II |
| 72 h 0.5% GA | 4% GS pH 9 | Paraben | 3 × 10 min NaCl | 32,950 | II |
| 72 h 0.5% GA | 4% AS pH 7 | Paraben | 3 × 10 min NaCl | 34,070 | II |
| 72 h 0.5% GA | 4% AS pH 3 | Paraben | 3 × 10 min NaCl | 49,890 E | I |
| Cell count in controls that were carried out in parallel | | | | 56,080 | I |

*glutaraldehyde
**glutamic acid
***All aftertreatments were for a period of 24 hours.

TABLE 2

| FIXATION | AFTERTREATMENT | STORAGE | WASHING | CELL COUNT 10th day | TOX |
|---|---|---|---|---|---|
| 72 h 0.5% GA* | *** | 0.25% GA | 3 × 10 min NaCl | 0 | V |
| 72 h 0.5% GA | — | 0.25% GA | 3 × 10 min PBS | 0 | V |
| 72 h 0.5% GA | — | 0.25% GA | 3 × 10 min HS | 0 | V |
| 72 h 0.5% GA | — | 0.25% GA | 3 × 1 d NaCl | 0 | V |
| 72 h 0.5% GA | — | 0.25% GA | 3 × 1 d PBS | 0 | V |
| 72 h 0.5% GA | — | Paraben | 3 × 10 min NaCl | 0 | V |
| 72 h 0.5% GA | PBS pH 7 | Paraben | 3 × 10 min NaCl | 0 | V |
| 72 h 0.5% GA | PBS | Paraben | 3 × 10 min NaCl | 0 | V |
| 72 h 0.5% GA | 0.5% NH3 | Paraben | 3 × 10 min NaCl | 0 | V |
| 72 h 0.5% GA | 4% GCl pH 7 | Paraben | 3 × 10 min NaCl | 0 | V |
| 72 h 0.5% GA | 4% GCl pH 7 10 min 1% NaBH4 | Paraben | 3 × 10 min NaCl | 0 | V |
| 72 h 0.5% GA | 4% Glycine pH 7 | Paraben | 3 × 10 min NaCl | 0 | V |
| 72 h 0.5% GA | 4% Glycine pH 3 | Paraben | 3 × 10 min NaCl | 0 | V |
| 72 h 0.5% GA | 4% GS** pH 7 | Paraben | 3 × 10 min NaCl | 0 | V |
| 72 h 0.5% GA | 4% G8 pH 3 | Paraben | 3 × 10 min NaCl | 124,420 E | I |
| 72 h 0.5% GA | 4% G8 pH 7 10 min 1% NaBH4 | Paraben | 3 × 10 min NaCl | 0 | V |
| 72 h 0.5% GA | 4% GS pH 9 | Paraben | 3 × 10 min NaCl | 0 | V |
| 72 h 0.5% GA | 4% AS pH 7 | Paraben | 3 × 10 min NaCl | 0 | V |
| 72 h 0.5% GA | 4% AS pH 3 | Paraben | 3 × 10 min NaCl | 113,560 E | I |

TABLE 2-continued

| FIXATION | AFTERTREATMENT | STORAGE | WASHING | CELL COUNT 10th day | TOX |
|---|---|---|---|---|---|
| Cell count in controls that were carried out in parallel | | | | 132,570 | I |

*glutaraldehyde
**glutamic acid
***All aftertreatments were for a period of 24 hours.

EXAMPLE 2

The 1 cm² pieces of bovine pericardium prepared in accordance with Example 1 were implanted, after a brief anesthesia, in 300 g Sprague Darley rats. For this purpose, 4 different materials were implanted randomly on the abdomen side of the animals. Each of the materials was implanted 7 times. After a period of 63 days, the materials were explanted and the calcium content of the samples was determined by means of atomic absorption spectroscopy. The results are given in micrograms of calcium/mg of dry weight in Table 3. A small sample was taken from the center of each of the preparations and subjected to a histological examination, the samples being stained by the method of Kossa with a special calcium phosphate stain. The samples were examined under a light microscope and assigned a HISTO score for the quantitative and qualitative occurrence of calcium.

III—Strong calcification of all layers of the materials, with destruction of a large part of the collagenous matrix.

II—Calcification of the central portions of the material, with maintenance, of a large portion of the collagenous matrix.

I—Very little occurrence of calcification, without visible destruction of the integrity of the collagenous matrix.

What we claim is:

1. A method of preparing a fixed biological implantation material, comprising:
   a) fixing a biological implantation material with an aldehyde, wherein said aldehyde is selected from the group consisting of glutaldenyde, formaldehyde, and glyoxal; and
   b) treating the fixed biological implantation material with an aminodicarboxylic acid in an acidic medium in the presence of a buffered medium, wherein the pH of said acidic medium is from 3 to 5, and wherein the concentration of said aminocarboxylic acid is from 0.001 M to 2.0 M.

2. The method of claim 1 where in the buffered medium is selected from sodium citrate/HCl, citrate-phosphate-borate/HCl and acetate.

3. The method of claim 1, wherein the aminodicarboxylic acid is in the form of an aqueous solution.

4. The method of claim 1 comprising carrying out the treating step for at least 2 hours at a constant temperature in the range of from 4° to 45° C.

5. The method of claim 1 further comprising storing the treated implantation material in a sterile solution.

6. The method of claim 1 wherein the aminodicarboxylic acid is selected from glutamic acid, aspartic acid, isomers, and mixtures thereof.

7. The method of claim 5 wherein the sterile solution consists essentially of 0.02% n-propyl p-hydroxybenzoate and 0.18% methyl p-hydroxybenzoate dissolved in a phosphate buffered salt solution.

TABLE 3

| FIXATION | AFTERTREATMENT | STORAGE | WASHING | ug Calcium/mg TG | HIST |
|---|---|---|---|---|---|
| 72 h 0.5% GA* | *** | 0.25% GA | 3 × 10 min NaCl | 169.05 ± 24.91 | III |
| 72 h 0.5% GA | | 0.25% GA | 3 × 1 d NaCl | 173.03 ± 34.89 | III |
| 72 h 0.5% GA | | Paraben | 3 × 10 min NaCl | 148.93 ± 36.98 | III |
| 72 h 0.5% GA | 4% GCl | Paraben | 3 × 10 min NaCl | 178.45 ± 34.98 | III |
| 72 h 0.5% GA | 4% Glycine pH 3 | Paraben | 3 × 10 min NaCl | 189.38 ± 36.87 | III |
| 72 h 0.5% GA | 4% Glycine pH 7 10 min 1% NaBH4 | Paraben | 3 × 10 min NaCl | 180.03 ± 67.89 | III |
| 72 h 0.5% GA | 4% Glycine pH 3 | Paraben | 3 × 10 min NaCl | 189.38 ± 45.57 | III |
| 72 h 0.5% GA | 4% GS** pH 7 | Paraben | 3 × 10 min NaCl | 145.78 ± 36.78 | III |
| 72 h 0.5% GA | 4% GS pH 3 | Paraben | 3 × 10 min NaCl | 13.65 ± 10.41 | I E |
| 72 h 0.5% GA | 4% GS pH 7 10 min 1% NaBH4 | Paraben | 3 × 10 min NaCl | 226.78 ± 78.48 | III |
| 72 h 0.5% GA | 4% GS pH 9 | Paraben | 3 × 10 min NaCl | 134.96 ± 36.78 | III |
| 72 h 0.5% GA | 4% AS pH 7 | Paraben | 3 × 10 min NaCl | 135.89 ± 17.07 | III |
| 72 h 0.5% GA | 4% AS pH 3 | Paraben | 3 × 10 min NaCl | 29.23 ± 7.05 | I E |

*glutaraldehyde
**glutamic acid
***All aftertreatments were for a period of 24 hours.

* * * * *